United States Patent [19]

Gordon et al.

[11] Patent Number: 5,191,505
[45] Date of Patent: Mar. 2, 1993

[54] ELECTRO-STATIC GROUNDING DEVICE

[75] Inventors: Michael E. Gordon, Boston; Lenard Cohen, Southboro; Paul Mills, Stow, all of Mass.

[73] Assignee: Plastic Systems, Inc., Marlboro, Mass.

[21] Appl. No.: 536,394

[22] Filed: Jun. 11, 1990

[51] Int. Cl.$^5$ .............................................. H05F 3/02
[52] U.S. Cl. .................................................. 361/223
[58] Field of Search ........................ 361/212, 220–224; 174/5 R, 5 G; 36/72 B, 72 R

[56] References Cited

U.S. PATENT DOCUMENTS 4,551,783  11/1985  Cohen et al. .......................... 361/223

*Primary Examiner*—A. D. Pellinen
*Assistant Examiner*—David Osborn
*Attorney, Agent, or Firm*—Hale and Dorr

[57] ABSTRACT

An electrostatic discharge foot grounding device made from a unitary piece of essentially planar conductive sheet material so that it includes, integrally connected, first and second leg portions and a connecting portion. The two leg portions form substantially a 90° angle with each other, and the connecting portion projects away from the second leg portion so that it and the leg portion form substantially a 135° angle with each other. Appropriate apertures in the leg portions and slits in the connecting portion provide attachment of the two leg portions into a generally cup-shaped configuration adapted to receive the heel or toe of a wearer's foot, and of the connecting portion to the cup so that, when the cup is placed on a wearer's foot, the connecting portion can be wrapped around the leg and attached to hold the cup in place.

16 Claims, 3 Drawing Sheets

ELECTRO-STATIC GROUNDING DEVICE

FIELD OF INVENTION

This invention relates to static control devices and, more particularly, to a limited use heel grounder for dissipating electro-static voltages on the body of the wearer to conductive flooring.

BACKGROUND OF INVENTION

One type of existing heel grounder (see, e.g., U.S. Pat. No. 4,551,783) includes a conductive rubber "cup" which fits onto the heel of a shoe and is held on the wearer's foot by an elastic or hook-and-loop fastener. The "cup" is connected to a conductive strip or tab which tucks into the wearer's sock or shoe. Devices of this type are typically very durable, lasting several months to over a year, but also are costly. Moreover, since the tab is in intimate contact with the wearer's foot, the grounder is rarely passed from one person to another. Rather, if one person (e.g., a visitor or temporary employee) no longer has any need for the device, it is typically thrown-away regardless of its condition.

To meet the need for a relatively short-term use device, disposable devices also have been provided. These typically provide a carbon-loaded polyethylene strip which adheres to the heel of a shoe and is tucked over into the shoe or sock to contact the wearer. Unfortunately, most products of this type suffer from a number of drawbacks. They frequently do not stay on the shoe very well, and tear easily. Thus, such "disposable" grounding devices often must be replaced several times a day, which reduces their cost advantage. More important, the failure or loss of the "disposable" grounder may not be immediately noticed, and there often will be some period of time during which the wearer will be unprotected.

There thus remains a need for a relatively low-cost device that avoids the drawbacks and shortcomings of available "disposable" grounders.

SUMMARY OF INVENTION

The present invention provides a single-piece, die-cut heel grounder that has the fit and functional characteristics of expensive, long-life devices, but that is much cheaper and more simple to manufacture. The device of the present invention also has a functional life that is long enough to insure that temporary users will receive full value, free from the worry of premature, unnoticed failure.

In particular, the present invention features an electrostatic discharge foot grounding device made from a unitary piece of essentially planar conductive sheet material so that it includes, integrally connected, first and second leg portions and a connecting portion. The two leg portions form substantially a 90° angle with each other, and the connecting portion projects away from the second leg portion so that it and the leg portion form substantially a 135° angle with each other. Appropriate apertures in the leg portions and slits in the connecting portion provide attachment of the two leg portions to form a generally cup-shaped configuration adapted to receive the heel or toe of a wearer's foot, and of the connecting portion to the cup so that, when the cup is placed on a wearer's foot, the connecting portion can be wrapped around the leg and attached to hold the cup in place.

DRAWINGS

DESCRIPTION OF PREFERRED EMBODIMENT

Figure 1:
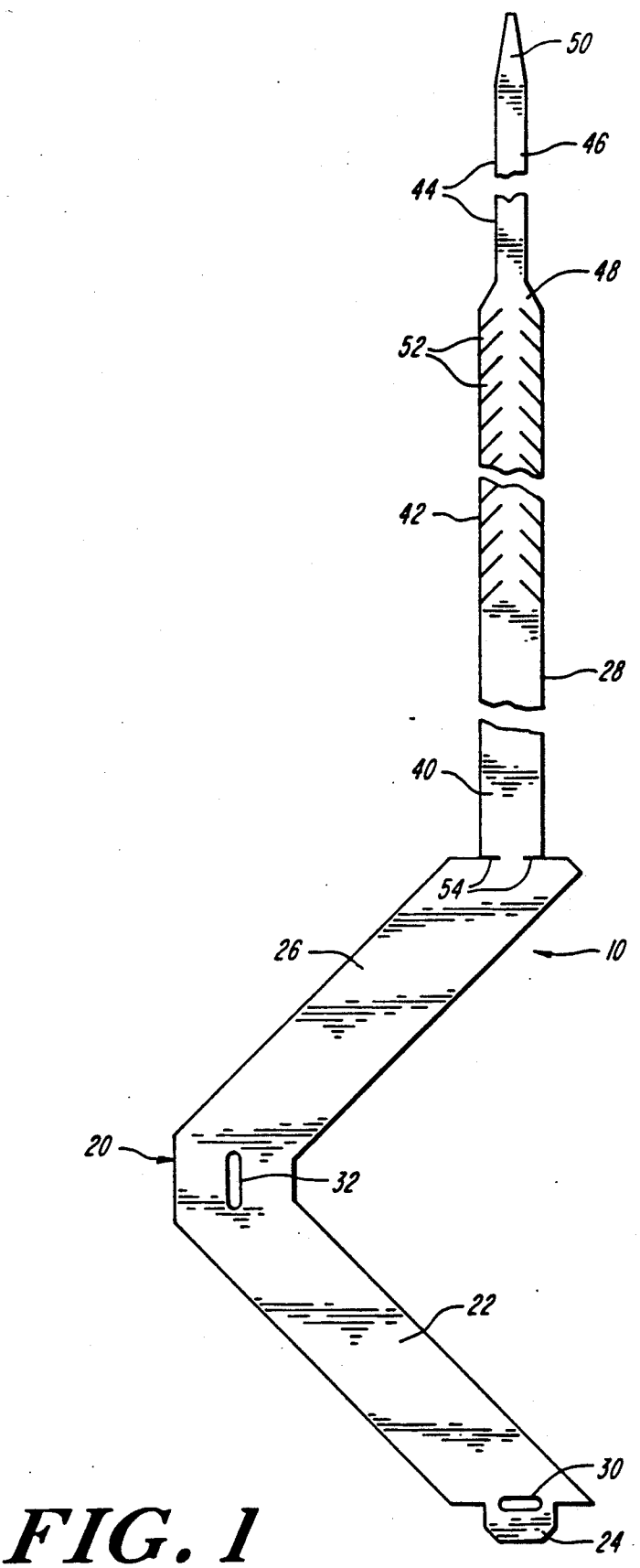
FIG. 1 is a plan view of an electro-static grounding device constructed in accord with the present invention.
Figure 2:
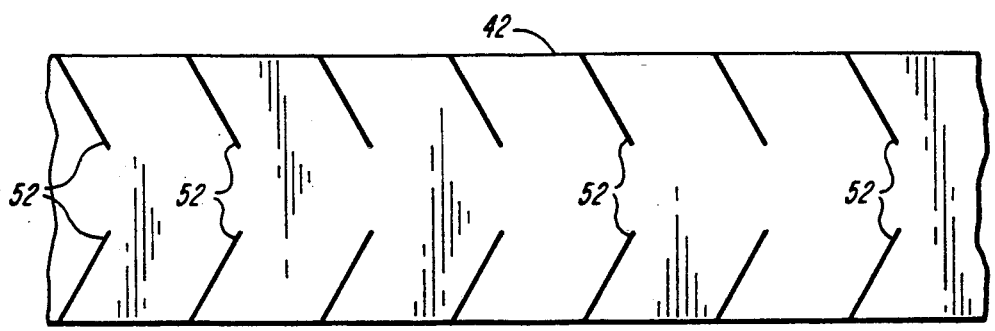
FIG. 2 is an enlarged view of a portion of the device of FIG. 1.

Referring now to FIGS. 1 and 2, there is shown a heel grounder, generally designated 10, comprising a single piece of vinyl-coated, conductive fabric. In a preferred embodiment, the fabric is carbon-loaded woven polyester about 15 mil thick, and is coated on each side with an about 5 mil thick layer of polyvinylchloride. Obviously, a number of different materials may be used so long as they have the desired mechanical (e.g., abrasion resistance and tear strength) and electrical (e.g., conductivity of about $10^6$ to $10^8$ ohms) properties.

As shown in FIG. 1, the heel grounder 10 includes an "L" shaped heel portion 20, one leg 22 of which is about 7 inches long and has a short rounded tab 24 projecting outwardly from its free end, and the other leg 26 of which is about 6 inches long and at its free end is attached to a projecting, almost 18 inches long, tab 28. Each of legs 22, 24 is about 1.12 in. wide.

As shown, tab 24 is oriented at 45° to leg 22 and a slot 30 (0.375 in. long ×0.187 in. wide) is provided at the junction of the leg and tab. A second slot 32 (0.312 in. long and 0.187 in. wide) is provided at the junction of leg 22 and leg 24, and is oriented at 45° to each of the legs.

The long tab 28 projects outwardly from the end of leg 26 (forming a 135° angle with leg 26) and includes a proximal portion 40 (5¼ in. long and ¾ in. wide), an intermediate connecting portion 42 (6.37 in. long and ¾ in. wide) and a generally tapered distal portion 44 (6 in. long). The distal tapered portion 44 includes a central section 46 of constant (approx. ⅛ in.) width between two tapering sections 48, 50. Connecting portion 42, shown most clearly in FIG. 2, includes eighteen pairs of identical, and identically oriented, slits 52, spaced about 0.37 in. apart along the length of the connecting portion. As shown, each slit 52 is oriented at an angle of 30° to leg 26, and extends inwardly about ¼ the width of the leg (i.e., the distance between the adjacent ends of the slits from the opposite sides of the leg is about 0.37 in.). Each pair of slits 52 thus forms the legs of a "V", with the open end of the "V" facing heel portion 20.

Another pair of slits 54 is provided on opposite sides of tab 28 at the junction between leg 26 and connecting tab 28.

As will be evident, a number of heel grounders may be die cut from a single sheet 100 of vinyl-coated fabric material. When properly laid out, the heel portions 20 of adjacent heel grounders will abut each other, and essentially the only material wasted will be at the ends of the sheet and in the thin strips between adjacent connecting tabs 28. A large number of heel grounders may be cut simultaneously, thus providing for extremely inexpensive manufacture.

The manner in which a heel grounder 20 is used by a wearer 200 is shown in FIGS. 3 and 4A–4D.

Figure 3:
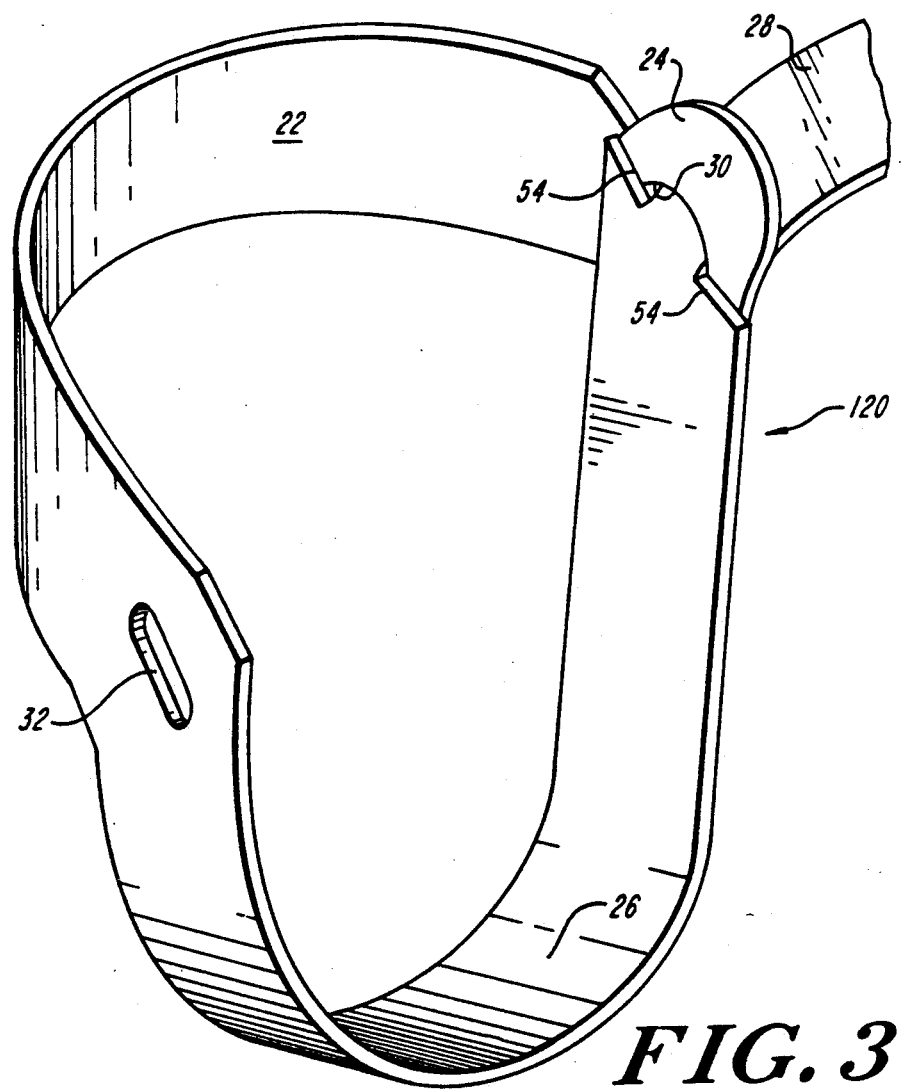
FIGS. 3 and 4A–4D illustrate use of the device of FIG. 1.

Initially, and as shown in FIG. 3, connecting tab 28 is drawn through slot 30 until at the end of leg 26 (to which tab 28 is attached) abuts the inside of the end of leg 22, with slots 54 engaging the fabric at either end of slot 30. As will be evident, this forms heel portion 22 into a "cup" 120 into which the heel (or, in the case of a woman's high-heeled shoe, the toe) of a shoe will fit.

As shown in FIGS. 4A-4D, the wearer's heel is placed in cup 120 (FIG. 4A) so that the bottom of the heel rests on leg 26 of heel portion 20 and the other leg 22 of the heel portion wraps around the back of the wearer's shoe.

Figure 4A:
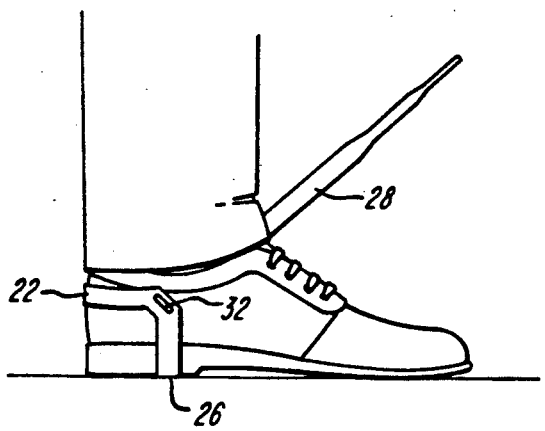
Figure 4B:
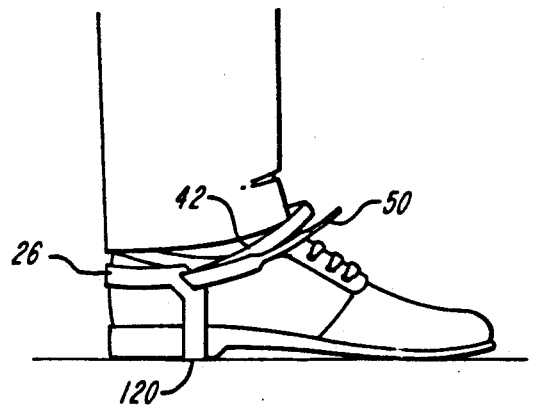
Figure 4C:
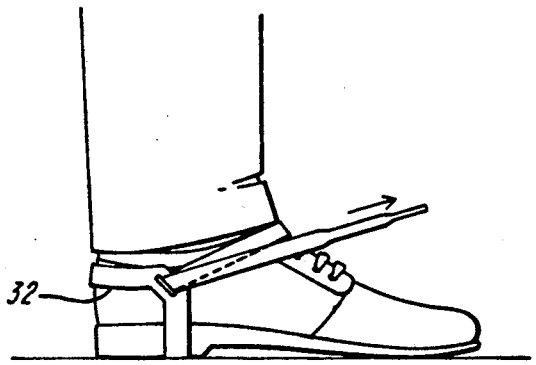
Figure 4D:
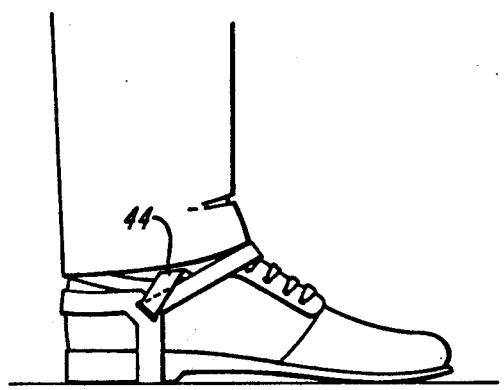

Long connecting tab 28 is then drawn over the front of the ankle, fed through slot 32 at the junction of legs 22, 26 of heel portion 20 (FIG. 4B), and drawn snug (FIG. 4C). The long tab 28 is held in place by a pair of slits 52, which engage the opposite sides of slot 32.

Finally, the distal portion 44 of connecting tab 28 is tucked into the wearer's shoe or sock (FIG. 4D) to provide the necessary electrical contact between the wearer and the floor.

Other embodiments will be within the scope of the following claims.

What is claimed is:

1. An electrostatic discharge control device consisting essentially of a unitary piece of conductive sheet material including:
   a first leg portion;
   a second leg portion integrally connected to and disposed at a substantial angle relative to said first leg portion, and
   a connecting portion integrally connected to said second leg portion at a point spaced from the point at which said second leg portion is connected to said first leg portion,
   said connecting portion projecting from said second leg portion in a direction extending generally away from said first leg portion and
   said device including
   first attachment means for attaching said first and second leg portions at a point spaced from that at which said leg portions are integrally connected to each other, and
   second attachment means for attaching said connecting portion to at least one of said first and second leg portions at a point spaced from that at which said connecting portion is integrally attached to said second leg portion,
   said first attachment means including an aperture in said device arranged to permit said connecting portion to be drawn therethrough, and a slit in said connecting portion arranged to engage opposite sides of said device adjacent said aperture, said aperture being located adjacent the end of said first leg portion most distant from the point at which said first leg portion is integrally connected to said second leg portion.

2. An electrostatic discharge control device consisting essentially of a unitary piece of conductive sheet material including:
   a first leg portion,
   a second leg portion integrally connected to and disposed at a substantial angle relative to said first leg portion, and
   a connecting portion integrally connected to said second leg portion at a point spaced from the point at which said second leg portion is connected to said first leg portion,
   said connecting portion projecting from said second leg portion in a direction extending generally away from said first leg portion and
   said device including
   first attachment means for attaching said first and second leg portions at a point spaced from that at which said leg portions are integrally connected to each other, and
   second attachment means for attaching said connecting portion to at least one of said first and second leg portions at a point spaced from that at which said connecting portion is integrally attached to said second leg portion,
   said second attachment means including an aperture in said device arranged to permit said connecting portion to be drawn therethrough, and a slit in said connecting portion arranged to engage opposite sides of said device adjacent said aperture, said aperture being located adjacent the point at which said first and second leg portions are integrally connected.

3. The device of claim 2 wherein said second attachment means includes a plurality of said slits spaced along a portion of the length of said connecting portion, each of said slits being oriented at an angle of about 45 degrees relative to the direction at which said connecting portion projects forms said second leg portion.

4. The device of claim 3 wherein a plurality of said slits are spaced along each side of said portion of the length of said connecting portion, and said slits are arranged so that pairs of slits form the sides of a "V" the open end of which faces towards the point at which said connecting leg portion projects from said second leg portion.

5. An electrostatic discharge foot grounding device consisting essentially of a single unitary piece of conductive sheet material including:
   a first leg portion;
   a second leg portion; and,
   a connecting portion,
   one end of said first leg portion being integrally connected to one end of said second leg portion and said leg portions forming substantially a 90° angle with each other,
   one end of said connecting portion being integrally connected to said second leg portion adjacent other end of said second leg portion and projecting from said second leg portion in a direction extending generally away from said first leg portion such that said second leg portion and said connecting portion form substantially a 135° angle with each other,
   first attachment means including a first aperture in said device adjacent the other end of said first leg portion for receiving said connecting portion and attaching said first and second leg portions to each other to form said first and second leg portions into a generally cup-shaped configuration adapted to receive the heel or toe of a wearer's foot, and
   second attachment means including a second aperture in said device adjacent the point of connection of said one ends of said first and second leg portions for receiving said connecting portion and attaching said connecting portion to at least one of said first and second leg portions such that when said device is formed in said cup-shaped configuration said connecting portion wraps around the wearer's leg and retains said device on the wearer's foot.

6. The device of claim 5 wherein said first attachment means includes a slit in at least one side of said connecting portion arranged to engage opposite sides of said device adjacent said aperture, said slit being located adjacent the point at which said connecting portion is integrally attached to said second leg portion.

7. The device of claim 6 wherein said second attachment means includes a plurality of slits spaced along opposite sides of a portion of the length of said connecting portion, each of said slits being oriented at an angle of about 45 degrees relative to the direction at which said connecting portion projects from said second leg portion and said slits being arranged in pairs such that each of said pairs forms the sides of a "V" the open end of which faces towards the point at which said connecting leg portion projects from said second leg portion.

8. The device of claim 7 wherein said connecting portion includes a first section adjacent said second leg portion, a second section including said slits, and a third tapered section said sections being integrally connected and longitudinally aligned.

9. The device of claim 5 wherein said sheet material includes a fabric impregnated with conductive carbon and coated with organic plastic.

10. The device of claim 9 wherein said organic plastic is polyvinylchloride.

11. The device of claim 5 wherein said sheet material has a conductivity in the range of $10^6$ to $10^8$ ohms.

12. An electrostatic discharge control device comprising a unitary piece of conductive sheet material including:
a first leg portion,
a second leg portion integrally connected to and disposed at a substantial angle relative to said first leg portion, and
a connecting portion integrally connected to said second leg portion at a point spaced from the point at which said second leg portion is connected to said first leg portion,
said connecting portion projecting from said second leg portion in a direction extending generally away from said first leg portion and
said device including
first attachment means including an aperture in said device at a point spaced from that at which said first and second leg portions are integrally connected to each other for attaching said first and second leg portions to each other to form said first and second leg portions into a generally cup-shaped configuration adapted to receive the heel or toe of a wearer's foot, and
second attachment means for attaching said connecting portion to at least one of said first and second leg portions at a point spaced from that at which said connecting portion is integrally attached to said second leg portion.

13. The device of claim 12 wherein said first attachment means includes a slit in said connecting portion arranged to engage opposite sides of said device adjacent said aperture.

14. The device of claim 12 wherein said second attachment means includes a second aperture in said device adjacent the point of connection of said one ends of said first and second leg portions for receiving said connecting portion.

15. The device of claim 14 wherein each of said first and second attachment means includes a respective slit in said connecting portion arranged to engage opposite sides of said device adjacent a respective one of said apertures.

16. The device of claim 12 wherein
said first and second leg portions are disposed substantially at a 90° angle to each other, and
said connecting portion is disposed substantially at a 45° angle to said second leg portion.

* * * * *